United States Patent
Van Driel et al.

(10) Patent No.: US 10,675,434 B2
(45) Date of Patent: Jun. 9, 2020

(54) SYSTEM AND A METHOD FOR IMPROVING A PERSON'S SLEEP

(71) Applicant: KONINKLIJKE PHILIPS N.V., Eindhoven (NL)

(72) Inventors: Jacqueline Van Driel, Eindhoven (NL); Joldert Maria Boersma, Groningen (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 991 days.

(21) Appl. No.: 14/359,463

(22) PCT Filed: Nov. 15, 2012

(86) PCT No.: PCT/IB2012/056444
§ 371 (c)(1),
(2) Date: May 20, 2014

(87) PCT Pub. No.: WO2013/076628
PCT Pub. Date: May 30, 2013

(65) Prior Publication Data
US 2014/0323799 A1 Oct. 30, 2014

Related U.S. Application Data

(60) Provisional application No. 61/562,120, filed on Nov. 21, 2011.

(51) Int. Cl.
*A61M 21/02* (2006.01)
*A61F 7/00* (2006.01)
(Continued)

(52) U.S. Cl.
CPC ............ *A61M 21/02* (2013.01); *A47C 21/048* (2013.01); *A47G 9/0215* (2013.01);
(Continued)

(58) Field of Classification Search
CPC ...... A61B 2562/0271; A61B 2562/046; A61B 5/1115; A61B 5/1126; A61B 5/4836;
(Continued)

(56) References Cited

U.S. PATENT DOCUMENTS

| | | |
|---|---|---|
| 4,433,062 A | 2/1984 | Courbin et al. |
| 4,633,062 A | 12/1986 | Nishida et al. |

(Continued)

FOREIGN PATENT DOCUMENTS

| | | |
|---|---|---|
| EP | 2269547 A1 | 1/2011 |
| JP | 2003061918 A | 3/2003 |

(Continued)

OTHER PUBLICATIONS

Enamul Hoque, "Monitoring Body Positions and Movements During Sleep using WISPs", Wireless Health, 10, Oct. 5-7, 2010, San Diego, USA, pp. 1-10.

*Primary Examiner* — Dana Ross
*Assistant Examiner* — James F Sims, III

(57) ABSTRACT

A system for improving a person's sleep includes a bedding layer having a plurality of individually controllable thermally adjustable zones, a plurality of temperature sensors, where at least one temperature sensor per thermally adjustable zone is dispersed throughout the bedding layer. Further, a controller is configured to control the heating power of each thermally adjustable zone, and detect in which the body presence is detected.

11 Claims, 2 Drawing Sheets

(51) Int. Cl.
*A61B 5/00* (2006.01)
*A61B 5/11* (2006.01)
*A47G 9/02* (2006.01)
*A47C 21/04* (2006.01)
*A61F 7/02* (2006.01)
*A61M 21/00* (2006.01)

(52) U.S. Cl.
CPC ........... *A61B 5/1115* (2013.01); *A61B 5/1126* (2013.01); *A61B 5/4836* (2013.01); *A61B 5/6892* (2013.01); *A61B 5/746* (2013.01); *A61F 7/007* (2013.01); *A61F 7/0097* (2013.01); *A47G 2200/166* (2013.01); *A61B 5/6891* (2013.01); *A61B 2562/0271* (2013.01); *A61B 2562/046* (2013.01); *A61F 2007/0001* (2013.01); *A61F 2007/0071* (2013.01); *A61F 2007/0093* (2013.01); *A61F 2007/0096* (2013.01); *A61F 2007/0295* (2013.01); *A61M 2021/0027* (2013.01); *A61M 2021/0044* (2013.01); *A61M 2021/0066* (2013.01)

(58) Field of Classification Search
CPC ..... A61B 5/6891; A61B 5/6892; A61B 5/746; A47G 2200/166; A47C 21/048; A47C 21/08
USPC ...................................... 600/27, 28; 219/212
See application file for complete search history.

(56) References Cited

U.S. PATENT DOCUMENTS

| | | | |
|---|---|---|---|
| 5,800,480 A | 9/1998 | Augustine et al. | |
| 5,948,303 A | 9/1999 | Larson | |
| 6,646,556 B1 | 11/2003 | Smith et al. | |
| 6,876,303 B2* | 4/2005 | Reeder | A61B 5/0002 340/573.1 |
| 8,525,680 B2* | 9/2013 | Riley | A61B 5/02055 340/573.1 |
| 2001/0020303 A1 | 9/2001 | Endo et al. | |
| 2006/0137099 A1* | 6/2006 | Feher | A47C 7/74 5/713 |
| 2006/0162074 A1 | 7/2006 | Bader | |
| 2007/0056101 A1* | 3/2007 | Mahajan | A61G 7/057 5/600 |
| 2009/0064411 A1 | 3/2009 | Marquette et al. | |
| 2009/0099630 A1 | 4/2009 | Augustine et al. | |
| 2009/0099631 A1 | 4/2009 | Augustine et al. | |
| 2009/0177257 A1 | 7/2009 | Khodak et al. | |
| 2010/0016016 A1 | 1/2010 | Brundage et al. | |
| 2011/0115635 A1* | 5/2011 | Petrovski | A47C 21/044 340/584 |
| 2011/0240751 A1* | 10/2011 | Rauh | B64D 13/00 236/91 D |
| 2011/0263950 A1 | 10/2011 | Larson et al. | |
| 2011/0289683 A1* | 12/2011 | Mikkelsen | A47C 21/048 5/421 |
| 2012/0053424 A1* | 3/2012 | Kenalty | A61B 5/0015 600/300 |

FOREIGN PATENT DOCUMENTS

| | | |
|---|---|---|
| JP | 2006516925 A | 7/2006 |
| WO | 03022190 A2 | 3/2003 |
| WO | 2006023479 A2 | 3/2006 |
| WO | 2009129306 A1 | 10/2009 |
| WO | 2010129803 A1 | 11/2010 |
| WO | 2012160502 A1 | 11/2012 |

* cited by examiner

SYSTEM AND A METHOD FOR IMPROVING A PERSON'S SLEEP

CROSS-REFERENCE TO PRIOR APPLICATIONS

This application is the U.S. National Phase application under 35 U.S.C. § 371 of International Application No. PCT/IB2012/056444 filed on Nov. 15, 2012, which claims the benefit of U.S. Provisional Patent Application No. 61/562,120 filed Nov. 21, 2011. These applications are hereby incorporated by reference herein.

FIELD OF THE INVENTION

The present invention relates to temperature adjustable bedding layers.

BACKGROUND OF THE INVENTION

Scientific studies have proven that a higher skin temperature in bed has a positive effect on the sleep of a person sleeping said bed. Scientific research has shown that warming the bed to get a small increase in skin temperature results in falling asleep faster, less awakenings during the night, longer sleeping time and more deep sleep.

Many people suffer from bad sleep. A survey in the USA in 2008 revealed that 65% of the adults experience bad sleep, stating that they have more than 2 nights a week not sleeping well. When these persons were asked for the reasons, they mentioned among other reasons that they have cold feet and/or feel either too warm or too cold during night.

Electrical blankets for raising the temperature in bed are well known and already exist for decades. However, the major disadvantage of conventional electric blankets is the fact that their temperature is not controlled. A constant power input is applied, and for some blankets the power setting can be changed in a few discrete steps. However, such a change of power setting does not take into account other conditions such as, for example, the presence of additional blankets on top of the bed, different metabolism of users in the bed or the room temperature. Thus, users of electric blankets often complain that the bed was heated too much during the night.

U.S. Pat. No. 4,433,062 describes a system that can detect the presence of a human body in the bed by a human body detection means for detecting retiring or rising of a user. The human body detection means is either pressure sensitive, or it may be a system using temperature signals in accordance with the presence or absence of a living human body. The preset temperature is automatically raised when the user rises so that the user is allowed to fall asleep again. The higher temperature preset is automatically decreased when the user goes to bed, and the presence of the user's body in the bed is detected.

US patent application publication US 2009/0099631 A1 discloses a multi-zone electric heating blanket which may be shaped to cover the outstretched arms or other body parts of a patient. The blanket includes two body part portions and a connecting bridge. A power controller may supply power to heating elements in both body part portions based on a temperature sensor in one of the body part portions. The temperature sensor is positioned such that it is always in direct contact with the patient's skin. The blanket comprises two temperatures sensors at maximum, and the temperature regulation is to prevent overheating.

Furthermore, in electric blankets, heat is supplied uniformly to the whole bed instead of being supplied to those areas only which in fact require heating. Blankets having a separate heating zone for the feet of a sleeping person exist, but again have a fixed heating power only rather than a temperature control.

There is a need for a bedding layer for improving a person's sleep, which bedding layer provides a better adjustment of the temperature within a bed.

More specifically, it is desirable to tune the temperature control of individual zones of the bedding separately accounting to the fact of whether a part of the sleeping person's body is lying on top or underneath an individual heating zone Therefore, it would be advantageous to detect the position of a body lying on a bed, without the need for direct contact between sensor and body. A solution could be to use pressure sensing mats that are commercially available. Such a pressure sensitive mat is placed underneath the body of a lying person, and the mat is capable of detecting a two-dimensional pressure distribution.

However, such mats are expensive, and not comfortable to lie as they are made of plastic-like material having limited flexibility and no moisture transmission.

SUMMARY OF THE INVENTION

The present invention utilizes temperature sensors within a bedding layer to detect the presence of a person in a bed, and/or the position of the person's body within the bed when a said person is present in the bed.

In a first aspect of the invention it is an objective to provide a method for improving a person's sleep. The method comprises detecting the presence and or the position of the body of the person on or underneath a bedding layer, the bedding layer comprising a plurality of individually thermally adjustable zones and a plurality of temperature sensors, wherein at least one temperature sensor per thermally adjustable zone is dispersed throughout the bedding layer, wherein any one of the group consisting of the temperature, the heating rate and the cooling rate of each thermally adjustable zone can be controlled separately, controlling any one of the group consisting of the temperature, the heating rate and the cooling rate of each individual thermally adjustable zone of the bedding layer such that the temperature of the thermally adjustable zones are adjusted to a preset temperature, and adjusting the temperature of each individual thermally adjustable zone of the bedding layer such that the temperature of each individual thermally adjustable zone in which areas a part of the person's body is present is maintained at a preset temperature.

In a second aspect of the invention it is an object to provide a system for improving a person's sleep, wherein the system can detect the presence and/or position of the person's body on or underneath the bedding layer and controls the temperature of individual thermally adjustable zones that are present in the bedding layer, accounting for the presence or absence of a part of the person's body in the area of each of the individual thermally adjustable zones. Thereby, it is possible to have a variation in temperature control of different parts of the bed environment, depending on the presence or absence of a part of the person's body. Temperature adjustment, e.g. heating or cooling of individual thermally adjustable zones can be turned off or on during night as the person moves in the bed and changes its body's position.

The system comprises a bedding layer comprising a plurality of thermally adjustable zones, a plurality of temperature sensors, wherein at least one temperature sensor per thermally adjustable zone is dispersed throughout the bedding layer. The thermally adjustable zones can be controlled separately, and means for controlling the heating power of each of said thermally adjustable zones depending on whether or not a part of the person's body is present in the area of said thermally adjustable zone.

It is a third aspect of the invention to provide a computer program product for improving a person's sleep, wherein the computer program includes a dedicated algorithm for detecting the position of a person's body on or underneath a bedding layer.

DETAILED DESCRIPTION OF EMBODIMENTS

Figure 1:
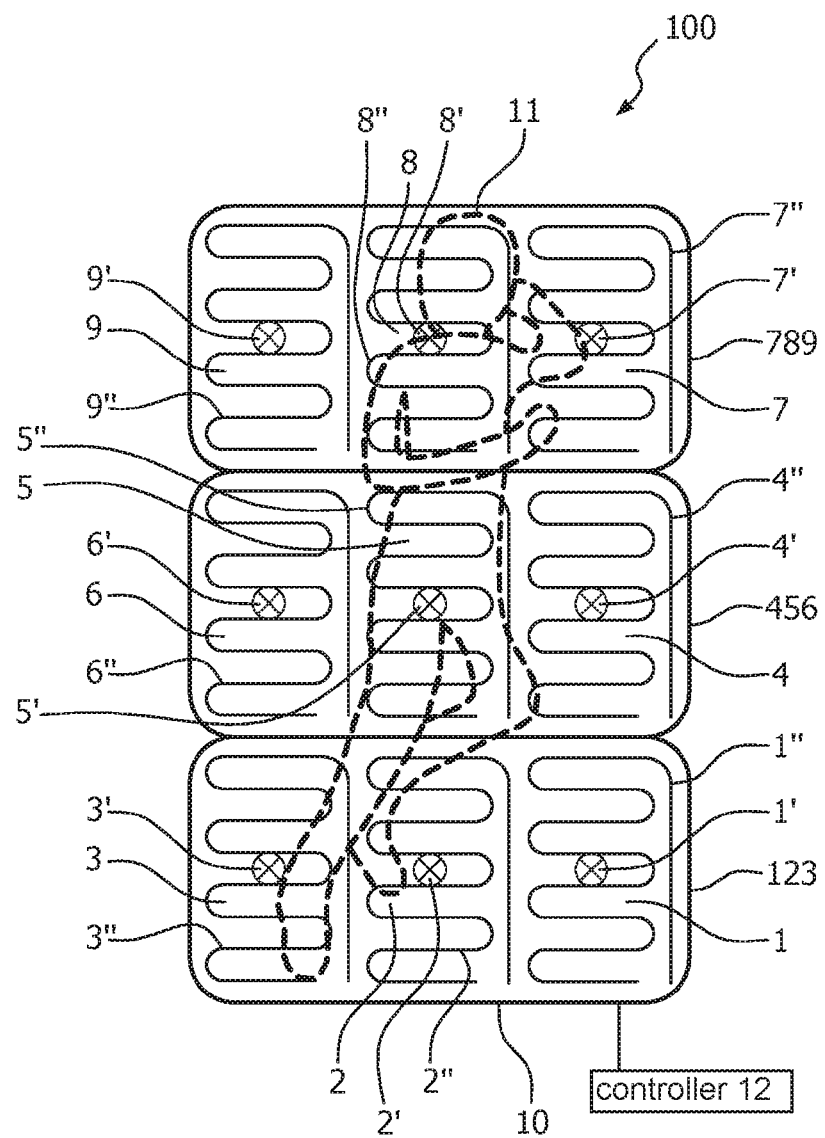
FIG. 1 illustrates a mattress according to one embodiment of the invention.

The present invention will be described with respect to particular embodiments and with reference to the figures, but the invention is not limited thereto, but only to the claims. The drawings described are only schematic and are non-limiting. In the drawings, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated. Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. Moreover, the terms top, bottom, over, under, beyond and the like in the description and in the claims are used for descriptive purposes and not necessarily for describing relative positions. It is to be understood that the terms so used are interchangeable under appropriate circumstances and that the embodiments of the invention described herein are capable of operation in other orientations than described or illustrated herein. It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

The method according to the first aspect of the invention comprises:
detecting the position of the body of the person on or underneath a bedding layer, the bedding layer comprising a plurality of individually thermally adjustable zones and a plurality of temperature sensors, wherein at least one temperature sensor per thermally adjustable zone is dispersed throughout the bedding layer, wherein any one of the group consisting of the temperature, the heating rate and the cooling rate of each thermally adjustable zone can be controlled separately,
controlling any one of the group consisting of the temperature, the heating rate and the cooling rate of each individual thermally adjustable zone of the bedding layer such that the temperature of the thermally adjustable zones are adjusted to a preset temperature, and
adjusting the temperature of each individual thermally adjustable zone of the bedding layer such that the temperature of each individual thermally adjustable zone in which areas a part of the person's body is present is maintained at a preset temperature.

The term "thermally adjustable" comprises being capable of cooling, heating and maintaining a temperature. "Thermally adjustable" or "thermally adjusted" further comprises influencing the heat loss to the environment.

In a non-limiting embodiment of the method, the bedding layer is a bedding layer according to one of the embodiments described in more detail for the first aspect of the invention.

In another or additional non-limiting embodiment, the method for detecting the position of the body of the person on or underneath the bedding layer comprises recording the temperature increase and/or the power required to maintain a set temperature.

The set temperature to be maintained in the method can preferably be set to a temperature between approximately 28° C. and 35° C. The temperature increases much faster in those areas of the bedding layer where the body of the person is in contact with the bedding layer, compared to those areas where the body is not in contact with the bedding layer. Also, in those areas of the bedding layer where the body of the person is in contact with the bedding layer, compared to those areas where the body is not in contact with the bedding layer, much less power is required to maintain the set temperature. Detecting the faster temperature increase to set temperature and/or the reduced need for maintaining the set temperature for each of the thermally adjustable zones is used to determine the zones in contact with the person's body, and hence is used to determine the position of the person's body on or underneath the bedding layer.

It is even possible that the actual temperature in close vicinity of the bedding layer, as determined by one or more of the temperature sensors, raises above the set temperature as the temperature of human skin is about 35.5° C., at least in some portions of the body. Thus, detecting that the actual temperature is above the set temperature of between approximately 28° C. to 35° C. is used to determine the position of the person's body on or underneath the bedding layer.

According to another or additional non-limiting embodiment of the method, the position of the body of the person on or underneath the bedding layer is determined in that the plurality of temperature sensors are used for identifying those thermally adjustable zones, where the temperature increases faster than in the other zones, where the power needed for maintaining a set temperature is less, compared to other thermally adjustable zones of the bedding layer, and where the actual temperature is above the set temperature.

In another or additional non-limiting embodiment of the method, the power for adjusting the temperature, e.g. the heating or cooling power, is adjusted to reach any one selected from the group consisting of rapid heating, rapid cooling, no over shooting of the temperature beyond or below the set temperature, no overheating, and no overcooling.

In another or additional non-limiting embodiment of the method, the protocol for thermal adjusting is different for those thermally adjustable zones where the presence of the person's body is not detected, and for those thermally adjustable zones where the person's body is detected. For example, the set temperature may be lower for the former thermally adjustable zones, but still within the comfortable temperature range, in particular for person's moving around during sleep, and higher for the latter thermally adjustable zones. As a person moves around in the bed during sleep or at night, these movements can also be detected in a preferred embodiment of the method. This information can be used for determining the sleep quality and can be given as feedback to the user of the system.

According to another or additional non-limiting embodiment of the method, the bedding layer is selected from the group consisting of bed sheets, blankets, and mattresses.

According to another or additional non-limiting embodiment of the method, the bedding layer comprises heating wires, and said temperature sensors are located between the electric heating wires.

According to another or additional non-limiting embodiment of the method, the bedding layer comprises tubes or channels, and said temperature sensors are located between these tubes or channels. Preferably, each thermally adjustable zone of the bedding layer comprises at least one tube or channel. Said at least one tube or channel constitutes of flow path for a cooling and/or heating medium. Said cooling medium is preferably selected from the group consisting of air and water.

According to another or additional non-limiting embodiment of the method, the bedding layer comprises at least one coolable zone, preferably a plurality of individually controllable coolable zones.

According to the second aspect of the invention, a system is provided which comprises a bedding layer comprising a plurality of thermally adjustable zones, a plurality of temperature sensors, wherein at least one temperature sensor per thermally adjustable zone is dispersed throughout the bedding layer, the temperature of each thermally adjustable zone can be controlled separately, and the system comprises means for controlling the heating or cooling power of each of said thermally adjustable zones, wherein the system is configured such that the position of the body of the person on or underneath the bedding layer can be detected, any one of the temperature, the heating rate and the cooling rate of each individual thermally adjustable zone can be controlled.

The system is configured that the means for controlling the heating or cooling power of the thermally adjustable zones can control the heating or cooling power of each of the thermally adjustable zones depending on whether or not a part of the person's body is present in the area of said thermally adjustable zone.

In a non-limiting embodiment of the system, the bedding layer is selected from the group consisting of bed sheets, blankets, and mattresses. The bedding layer may be a bed sheet that is used by the person to cover his/her body while lying in bed. This embodiment has the advantage that the person can take the bedding layer wherever he or she wants to sleep. The bedding layer of this embodiment is not restricted to a specific bed, but can be transferred to any other bed, sofa or the like said person wants to rest or sleep.

In preferred embodiments, the bedding layer is a blanket or mattress. In these embodiments, the bedding layer is a bedding layer that is intended for a person to lie on while resting or sleeping. Being configured as blanket or mattress, the bedding layer according to this embodiment provides the advantage of a more accurate detection of the person's body position in bed.

In another or additional non-limiting embodiment of the system, the bedding layer comprises heating means, preferably electric heating wires, and the temperature sensors are located between the electric heating wires. Using electric heating wires for heatable blankets is known in the art. Using multiple electric heating wires for the bedding layer allows providing each individual heatable zone with an individual electric heating wire such that each individual heatable zone can be heated individually. Thus, the bedding layer of this embodiment comprises multiple individual heatable zones, and multiple individual electric heating wires, wherein each individual heatable zone includes at least one electric heating wire. Thereby, each of the individual heatable zones can be heated separately in that electric power is applied to the electric heating wire of said individual heatable zone.

In another or additional non-limiting embodiment, the bedding layer comprises combined cooling and heating means. Said cooling and heating means are preferably selected from the group consisting of tubes and channels. A heat transferring medium such as water or air can be forced to flow through the tubes or channels. The temperature sensors are located between the heating and cooling means. Using multiple tubes or channels allows separation of the bedding layer in multiple individually thermally adjustable zones. By addressing each channel with an individual fluid flow that is heated or cooled, the temperature of each zone can be controlled independently.

The bedding layer of this embodiment further includes multiple temperature sensors, at least one temperature sensor for each individual thermally adjustable zone, wherein each of the temperature sensors is located in between, but not in direct contact with the heating/cooling means. This arrangement provides the most accurate opportunity of sensing the temperature in the area of the thermally adjustable zone where said temperature sensor is located, and at the same time sense the heat coming from or the temperature of the person's body. In addition, this arrangement permits an accurate determination of whether a part of the person's body is present in the area of a specific individual thermally adjustable zone or not. Hence, this arrangement permits a good spatial resolution of the person's body position in bed.

In a non-limiting embodiment of the system, the bedding layer can be heated and/or cooled. Preferably, the bedding layer comprises a plurality of thermally adjustable zones. Providing the bedding layer with one or more thermally adjustable zones, the microclimate of the bed can be adjusted more individually and/or over a broader range. This embodiment has the advantage of decreasing the amount of energy needed for cooling, as the coolable zone is only cooled when the presence of a person or a body part is detected. This embodiment also permits the use of the system in case the environmental temperature is such that heating the bed would be considered uncomfortable by a given person. In a preferred embodiment, the plurality of coolable zones can be individually controlled. The embodiment provides the advantage that the bedding layer allows spatially distinct cooling of the bedding layer, preferably depending on whether or not a part of the person's body is present in the area of a coolable zone or not.

In an embodiment of the system, each individual thermally adjustable zone is an individually controllable coolable zone too. This embodiment provides that the temperature of each of these individual zones can be controlled at the best possible extent, i.e. the range of temperatures the desired temperature can be adjusted to is larger, the speed of raising or lowering the temperature in the zone is faster, the likelihood of overheating is reduced, because it can be prevented by active means, and the like.

In a further or additional non-limiting embodiment, the system is configured to trigger an alarm when a person gets out of it bed. The system can detect the presence or absence of a living person in a bed by means of the temperature sensors the bedding layer is provided with.

When all or at least more than a predetermined number of the temperature sensors detects a decreasing temperature or a temperature below the temperature caused by a living person in the bed and/or a temperature within the range of the ambient temperature in the bedroom, the system may trigger an alarm. In an embodiment, the alarm may be given to a caretaker who takes care of the person supposed to be in bed. This embodiment is particularly useful in facilities where persons live which need to be taken care of such as disabled, mentally disabled or imprisoned persons, or persons suffering from senile dementia. Any caretaker can be notified promptly if one of the persons to be taken care of has left the bed, purposely or not, and can look after that person.

In a further or additional non-limiting embodiment, the system is configured for detecting the time a person is out of the bed. In this embodiment, the system can not only detect the presence or absence of a living person in a bed by means of the temperature sensors the bedding layer is provided with, but also records the time a person is out of its bed. This configuration permits delaying an alarm to be triggered such that not every short-term leaving of the bed will cause an alarm which may classify as a false alarm. This embodiment may further assist in switching-off the system in case that the heating is no longer needed. For example, recording the time a person is out of its bed may be utilized to determine whether said person got up and started his daily routine. During the daily routine, the heating of/by the bedding layer is not required, and the system can be shut-off to save energy and for safety reasons as well.

Also for the realization of the sleep benefit it is important to know that the user is temporarily out of the bed. Otherwise the loss of body heat input in the bed might result in compensation by the system resulting in possible overshoot once the user returns.

In a further or additional non-limiting embodiment, the system is configured to automatically switch-off the heating after a preset period of time after the person got out of the bed. In the embodiments which automatically switch-off the system, no manual switching-off each day is required, and switching-off cannot be forgotten.

In a further or additional non-limiting embodiment, the system is configured to record the movements of the person during night. The information of the person's movement at night can be used to provide a feedback to the person about the duration, intensity, depth and quality of sleep, and may hence be used by the person to further improve the quality of his sleep, for example in adjusting the preset temperature of the system to a more comfortable temperature.

In a further or additional non-limiting embodiment, the system is configured to adjust local bed properties other than temperature. The adjustment of other properties than the temperature, in addition to controlling the temperature, can help improving the sleep quality of a person. An examples of other properties than temperature that can be adjusted by the system according to this embodiment is the stiffness of the mattress. Other properties may for example be the position of the upper end of the mattress, the position of the lower end of the mattress, for example in height of the feet and/or knees, the illumination of the bedroom, the positioning of shades in front of the bedroom windows, the presence and/or loudness of background music, the environmental temperature in the bedroom, the intensity of ventilation of the bedroom, the insulation properties of the bedding material, and the like.

FIG. 1 illustrates an embodiment of the system 100. The system 100 comprises a mattress 10, wherein said mattress 10 comprises three sections 123, 456, and 789. A first section 123 constitutes the foot end of the mattress, a second section 456 constitutes the midsection of the mattress, and a third section 789 constitutes the head end of the mattress. Each of the three sections 123, 456, and 789 comprises three zones, wherein section 123 comprises zones 1, 2 and 3, section 456 comprises zones 4, 5 and 6, and section 789 comprises zones 7, 8 and 9. Each zone N, wherein N represents an integer from 1 to 9, comprises a temperature sensor N' and a means N" for adjusting the temperature of the zone N' said means N" is located in. Said means N" for adjusting the temperature of a zone N' may for example be an electric heating wire and/or a tube filled with a heating/cooling medium such as air or water. For example, section 123 includes zone 1. Said zone 1 comprises a temperature sensor 1' for detecting the temperature in zone 1, and a means 1" for adjusting the temperature in zone 1. The system 100 allows adjusting the temperature of each zone N for a person 11 lying on the mattress.

Figure 2:
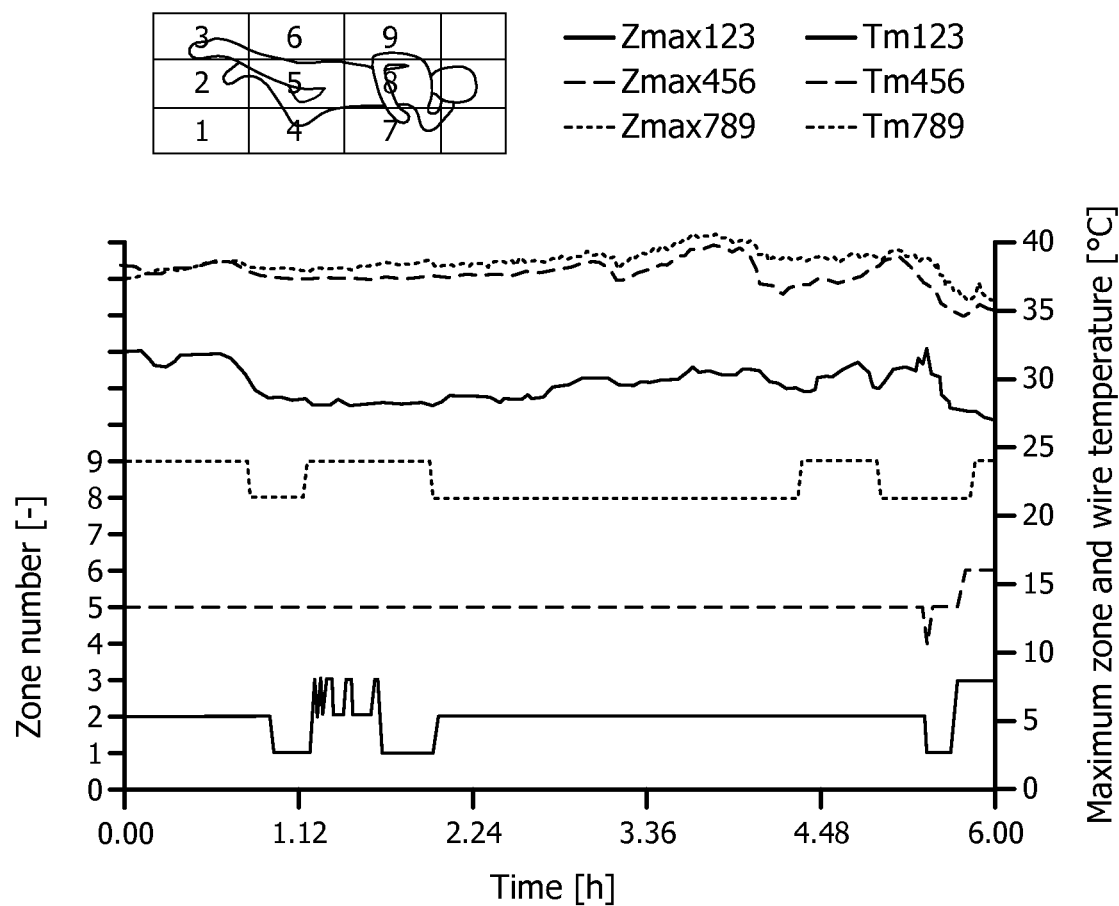
FIG. 2 is a diagram illustrating the body position of a sleeping person relative to individual mattress zones, and a graph showing body position as a function of time as well as maximum temperatures in various zones.

FIG. 2 is a diagram illustrating the body position in a bed based on maximum temperatures in individual zones N of a mattress. The signals were measured in a sleep laboratory test and indicate the position of a sleeping person's body. The left axis indicates where parts of the person's body were positioned as a function of time during one night. As can be seen from the solid line, the persons' feet moved between zones 1, 2 and 3 (see sketch above the graphs), but were most of the time in zone 2. The person's hips were mainly in zone 5 (dashed line). The shoulders of said person were mainly in zones 8 and 9 (dotted line).

The graphics in FIG. 2 also shows the maximum temperatures that were measured in zones 1, 2, 3 (solid line), in zones 4, 5, 6 (dashed line), and in zones 7, 8, and 9 (dotted line), wherein the right axis indicates the temperatures.

In the third aspect, the invention provides a computer program product for improving a person's sleep, wherein the computer program includes an algorithm for detecting the position of a body on or underneath a bedding layer. The algorithm uses the knowledge of at least one of the group consisting of the set temperature, the room temperature, the human metabolic rate, skin temperature, and at least one of the difference in temperature change with or without a person present, the difference in power consumption for maintaining a set temperature with or without a person present, and the actual temperature, with respect to each one of the plurality of temperature sensors. The algorithm when executed by a controller 12 uses this information in controlling the heating or cooling power applied to each of the individual thermally adjustable zones.

In an embodiment, the algorithm of the computer program further controls the cooling power applied to each of the individual cooling zones.

The invention claimed is:

1. A system for improving sleep of a person sleeping on a bed, the system comprising:
   a bedding layer comprising a plurality of zones;
   a means for heating or cooling the plurality of zones, the plurality of zones being thermally adjustable;

temperature sensors configured to sense temperatures of the plurality of zones, wherein at least one temperature sensor per thermally adjustable zone is dispersed throughout the bedding layer; and a controller configured to execute an algorithm, wherein when the algorithm is executed, the controller is configured to:

detect a position of a body of the person on or underneath the bedding layer using the temperature sensors, control temperature of each of the plurality of zones based on presence or absence of a part of the body of the person in an area of each thermally adjustable zone of the plurality of zones, the each thermally adjustable zone being controlled separately, and increase a speed of raising and lowering the temperature of the each thermally adjustable zone by controlling a heating rate or a cooling rate of the each thermally adjustable zone of the plurality of zones.

2. The system according to claim 1, wherein the bedding layer is selected from a group consisting of bed sheets, blankets, and mattresses.

3. The system according to claim 1, wherein the bedding layer includes the means for heating or cooling, wherein the means for heating or cooling includes electric heating wires, and wherein the temperature sensors are located between the electric heating wires.

4. The system according to claim 1, wherein the means for heating or cooling are selected from a group consisting of tubes and channels, and the temperature sensors are located between the tubes and channels, and wherein the means for cooling or heating circulates a cooling medium in the tubes and channels.

5. The system according to claim 1, wherein the plurality of zones include a plurality of individually controllable thermally adjustable zones.

6. The system according to claim 1, wherein the controller is configured to control a cooling power of the plurality of zones.

7. The system according to claim 1, wherein the controller is configured to trigger an alarm when the person gets out of the bed.

8. The system according to claim 1, wherein the controller is configured to record a time the person is out of the bed.

9. The system according to claim 1, wherein the controller is configured to record movements of the person on the bed.

10. The system according to claim 1, wherein the controller is configured to adjust at least one local bed environmental property other than temperature of the bedding layer, the at least one local bed environmental property other than temperature being selected from a group consisting of: mattress stiffness, illumination of the bedroom, positioning of shades, loudness of background music, environmental temperature, intensity of ventilation, insulation properties of bedding material, and a combination thereof.

11. The system according to claim 1, wherein the controller is configured to automatically switch-off the power after a preset period of time after the person gets out of the bed.

* * * * *